United States Patent
Karusala et al.

(10) Patent No.: US 8,530,647 B2
(45) Date of Patent: Sep. 10, 2013

(54) PROCESS FOR THE PREPARATION OF OXCARBAZEPINE

(75) Inventors: Nageswara Rao Karusala, Hyderabad (IN); Uma Sankara Sastry Tummalapally, Hyderabad (IN); Appi Reddy Talatala, Hyderabad (IN); Debashish Datta, Hyderabad (IN)

(73) Assignee: Mylan Laboratories Limited (IN)

( * ) Notice: Subject to any disclaimer, the term of this patent is extended or adjusted under 35 U.S.C. 154(b) by 131 days.

(21) Appl. No.: 12/991,600

(22) PCT Filed: May 6, 2009

(86) PCT No.: PCT/IN2009/000272
§ 371 (c)(1),
(2), (4) Date: Nov. 8, 2010

(87) PCT Pub. No.: WO2009/139001
PCT Pub. Date: Nov. 19, 2009

(65) Prior Publication Data
US 2011/0065917 A1    Mar. 17, 2011

(30) Foreign Application Priority Data

May 8, 2008  (IN) ............................ 1135/CHE/2008
Jul. 10, 2008  (IN) ............................ 1678/CHE/2008

(51) Int. Cl.
*C07D 223/26*   (2006.01)

(52) U.S. Cl.
USPC ........................................................ 540/589

(58) Field of Classification Search
USPC ........................................................ 540/589
See application file for complete search history.

(56) References Cited

U.S. PATENT DOCUMENTS

| 3,642,775 A | 2/1972 | Schindler et al. |
| 5,808,058 A | 9/1998 | Milanese |
| 6,670,472 B2 | 12/2003 | Ansari et al. |
| 7,015,322 B1 | 3/2006 | Eckardt et al. |
| 2005/0203297 A1 | 9/2005 | Sivakumar et al. |
| 2007/0032647 A1 | 2/2007 | Parenky et al. |

FOREIGN PATENT DOCUMENTS

| EP | 1600443 A1 | 11/2005 |
| WO | 9621649 A1 | 7/1996 |

OTHER PUBLICATIONS

International Search Report, PCT/IN2009/000272 dated Dec. 2, 2010.

*Primary Examiner* — Brenda Coleman
(74) *Attorney, Agent, or Firm* — Lerner, David, Littenberg, Krumholz & Mentlik, LLP

(57) ABSTRACT

The present invention relates to an improved process for the preparation of 10-oxo-10,11-dihydro-5H-dibenz[b,f]azepine-5-carboxamide (Oxcarbazepine) by reacting 10-methoxy-5H-dibenz[b,f]azepine (10-methoxyiminostilbene) and alkali metal cyanate in presence of α-hydroxy acids, and also relates to the process for the preparation of carbamazepine from iminostilbene. Further the present invention is directed to the novel crystalline form of 10-methoxy carbamazepine.

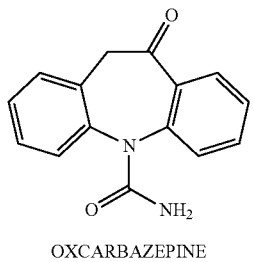

OXCARBAZEPINE (I)

13 Claims, 1 Drawing Sheet

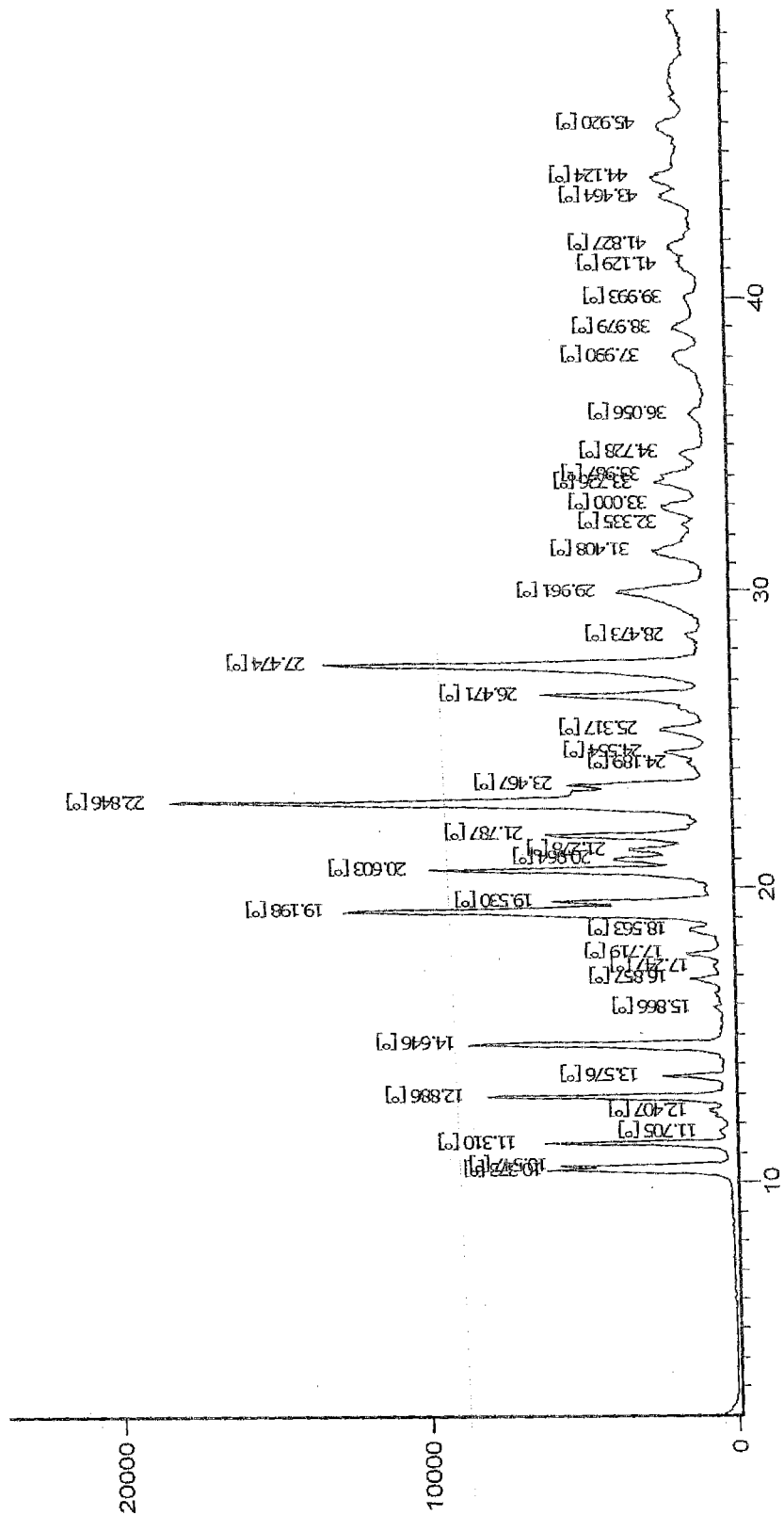

PROCESS FOR THE PREPARATION OF OXCARBAZEPINE

CROSS REFERENCE TO RELATED APPLICATIONS

The present application is a national phase entry under 35 U.S.C. §371 of International Application No. PCT/IN2009/000272, filed May 6, 2009, published in English, which claims the benefit of Indian Patent Application Nos. 1135/CHE/2008, filed May 8, 2008 and 1678/CHE/2008 filed Jul. 10, 2008. The disclosures of said applications are incorporated by reference herein.

FIELD OF THE INVENTION

The present invention relates to an improved process for the preparation of 10-oxo-10,11-dihydro-5H-dibenz[b,f]azepine-5-carboxamide (Oxcarbazepine) from 10-methoxy-5H-dibenz[b,f]azepine (10-methoxyiminostilbene) and also relates to a process for the preparation of carbamazepine from iminostilbene. Further, the present invention relates to crystalline 10-methoxy carbamazepine.

BACKGROUND OF THE INVENTION

Oxcarbazepine is chemically known as 10-oxo-10,11-dihydro-5H-dibenz[b,f]azepine-5-carboxamide and represented by the following structural formula:

OXCARBAZEPINE

Oxcarbazepine is commercially available as TRILEPTAL®, which has been approved by the United States Food and Drug Administration for use in the treatment of epilepsy and use as monotherapy or adjunctive therapy in the treatment of partial seizures in adults and as monotherapy in the treatment of partial seizures in children.

U.S. Pat. No. 3,642,775 assigned to Ciba-Geigy Corporation, claims Oxcarbazepine specifically and discloses the process for the preparation of Oxcarbazepine, wherein 10-methoxy-5H-dibenz[b,f]azepine is reacted with phosgene gas to give 10-methoxy-5H-dibenz[b,f]azepine-5-carbonyl chloride and ammonolysis of the resultant compound to give the amide followed by hydrolysis to give Oxcarbazepine.

U.S. Pat. No. 5,808,058 assigned to Trifarma S.r.l., claims a process for the preparation of Oxcarbazepine by carbomylating 10-methoxyiminostilbene with sodium or potassium cyanate in the presence of strong non-aqueous acid, followed by mild aqueous acid hydrolysis of the methoxy group.

U.S. Pat. No. 6,670,472 B2 assigned to Max India Limited, claims a process for the preparation of Oxcarbazepine, which comprises reacting 10-methoxyiminostilbene with cyanic acid generated in situ by reaction of an alkali metal cyanate and a mild aromatic acidic reagent such as benzoic acid, the obtained 10-methoxycarbamazepine may then be hydrolyzed to form Oxcarbazepine. The major disadvantage of this process is the reported yields are very low, of about 28-49%.

US 2005/0203297 A1 assigned to Glenmark Pharmaceuticals, claims a process for the preparation of 5H-dibenz[b,f]azepine-5-carboxamide by reacting 5H-dibenz[b,f]azepine with one or more alkali or alkaline-earth cyanates in the presence of one or more unsaturated dicarboxylic acid. But, this process involves number of purification.

In the prior art processes, cyanic acid is generated by reaction of alkali metal cyanates in the presence of acid with or without electron with-drawing groups. The starting material (10-methoxy iminostilbene) is sensitive to acids, due to more acidic nature of the acid the starting material may decompose and more degradation impurities are obtained in the prior art processes. We identified a new class of acid compounds i.e., α-hydroxy acids, where the hydroxyl is a electron releasing group at α-position, this influences the basicity of the acid. So these acids are less acidic than the reagents claimed in the prior art and less by-products are expected in the reaction.

According to the prior processes, strong acids are used for both the carbomylation reaction and the hydrolysis reaction. These acids are actively involved in ether hydrolysis to form substantial quantities of byproducts, i.e., oxo-iminodibenzyl or lead to degradation of the product and result in substantial quantities of impurities. Due to formation of impurities, repeated purifications in different solvents are needed to give the desired quality of the final product.

The major disadvantage as per prior art processes is incomplete hydrolysis of the starting material. According to the prior art processes, 10-methoxycarbamazepine content, while hydrolysis reaction is around 3%. The removal of 10-methoxy carbamazepine from the final API requires a number of purifications in different solvents. Whereas, the present invention provides a hydrolysis reaction in which the starting material content is less than 1%, preferably less than 0.5%. Therefore the present invention provides Oxcarbazepine with improved yields and quality. The present invention also provides the API with good color when compared to the product obtained by prior art processes.

Therefore, there is a need to develop a process for the preparation of Oxcarbazepine, which is economical and results in high yields. The present invention will overcome the deficiencies of the prior art and provide a higher yielding, cost-effective and scalable process for the commercial production of highly pure Oxcarbazepine.

OBJECT OF THE INVENTION

The main object of the present invention is to provide an improved process for the preparation of Oxcarbazepine.

Yet another object of the present invention is to provide an improved process for the hydrolysis of 10-methoxy carbamazepine in presence of organic acid to produce Oxcarbazepine.

Another object of the present invention is to provide an improved process for the preparation of Carbamazepine.

Another object of the present invention is to provide an improved process for the preparation of Licarbazepine.

Another Main object of the present invention is to provide crystalline 10-methoxy carbamazepine.

SUMMARY OF THE INVENTION

It is the principal aspect of the present invention to provide an improved process for the preparation of 10-methoxy carbamazepine wherein 10-methoxyiminostilbene is reacted with alkali metal cyanate and α-hydroxy acid to give 10-methoxy carbamazepine.

Another aspect of the present invention is to provide a process for the preparation of carbamazepine wherein iminostilbene is reacted with alkali metal cyanate and α-hydroxy acid to give carbamazepine.

Furthermore, the present invention is also directed to the process for the preparation of Oxcarbazepine wherein 10-methoxyiminostilbene is reacted with alkali metal cyanate and α-hydroxy acid to give 10-methoxy carbamazepine. It is optionally subjected to crystallization in a solvent medium followed by hydrolysis in presence of an acid to give pure Oxcarbazepine.

Yet another aspect of the present invention is to provide a process for the preparation of Licarbazepine by reacting Oxcarbazepine with a reducing agent.

The main aspect of the present invention is to provide crystalline 10-methoxy carbamazepine.

BRIEF DESCRIPTION OF THE DRAWINGS

Further description of preferred embodiments of the invention which are shown in the accompanying drawing figures, wherein:

FIG. 1 illustrates the powder XRD pattern of crystalline 10-methoxy carbamazepine.

DETAILED DESCRIPTION OF THE INVENTION

The present invention relates to an improved process for the preparation of (Oxcarbazepine), wherein 10-methoxyiminostilbene is reacted with alkali metal cyanates in the presence of α-hydroxy acid to give 10-methoxy carbamazepine, which is subjected to hydrolysis reaction in the presence of organic acid to give Oxcarbazepine with improved yield and quality.

The present invention also relates to improved process for the preparation of carbamazepine, wherein iminostilbene is reacted with alkali metal cyanates in the presence of α-hydroxy acid to give Carbamazepine.

The present invention relates to an improved process for the preparation of Oxcarbazepine which comprises the steps of: (a) reacting 10-methoxy iminostilbene with alkali metal cyanate and α-hydroxy acid in solvent, (b) isolating 10-methoxy carbamazepine, (c) optionally crystallizing the 10-methoxy carbamazepine, (d) hydrolyzing the 10-methoxy carbamazepine in acid and (e) isolating Oxcarbazepine.

Accordingly, the present invention provides an improved process for the preparation of Oxcarbazepine, wherein 10-methoxy iminostilbene is reacted with alkali metal cyanate and α-hydroxy acid in a solvent medium to give 10-methoxy carbamazepine. The alkali metal cyanate is selected from sodium cyanate, potassium cyanate. α-hydroxy acid is selected from glycolic acid, lactic acid, citric acid, tartaric acid, mandelic acid or mixtures thereof. The preferred α-hydroxy acid is mandelic acid.

According to the present invention, the carbomylation reaction is carried in a solvent selected from dichloromethane, dichloroethane, toluene, hexane, heptane cyclohexane, or mixtures thereof. The preferred solvent is dichloromethane. The isolated 10-methoxy carbamazepine is subjected to optionally crystallization in a solvent selected from methanol, ethanol, propanol, isopropyl alcohol, water or mixtures thereof.

According to the present invention the hydrolysis of 10-methoxy carbamazepine is carried out in the presence of an acid in solvent. The acid is selected from organic acid such as oxalic acid, formic acid, preferably oxalic acid. The solvent used for the hydrolysis reaction is selected from group comprising of water, water miscible organic solvent, water immiscible organic solvents or mixtures thereof. The water miscible organic solvent is selected from methanol, ethanol, propanol, isopropanol, butanol, t-butanol, tetrahydrofuran (THF), dimethyl formamide (DMF), dimethyl sulfoxide (DMSO), and acetonitrile. The water immiscible solvents are selected from the group of benzene, hexane, toluene, methylene dichloride, ethylene dichloride, chloroform, cyclohexane, and xylene. The preferred solvent for hydrolysis is water.

According to our present invention, Oxcarbazepine synthetic scheme is as given below.

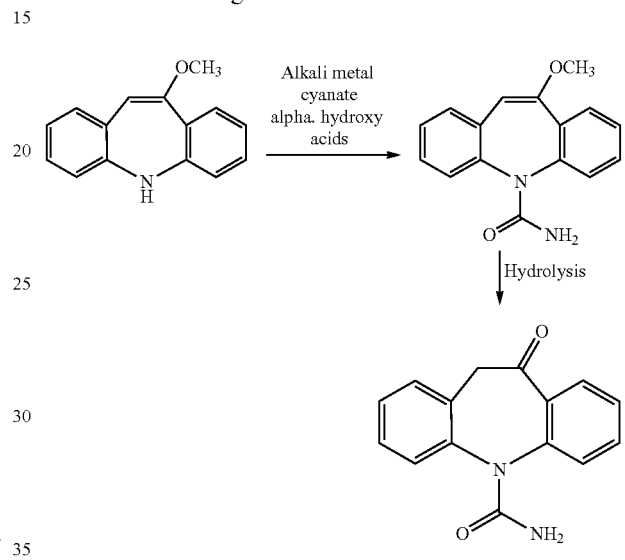

According to one embodiment of the present invention the hydrolysis of 10-methoxy carbamazepine to produce Oxcarbazepine can be carried out as per the conventional methods, for example as described in U.S. Pat. No. 5,808,058, US 2005-0203297 A1, US 2007-0032647 A1.

According to one aspect of the present invention, the purification of Oxcarbazepine is carried out in presence of a solvent selected from water, methanol, ethanol, propanol, isopropanol, butanol or mixtures thereof.

According to another aspect of the present invention purification of Oxcarbazepine is carried out in the presence of a solvent mixture of methanol and methylene dichloride (MDC).

One more aspect of the present invention is to provide improved process for the preparation of Carbamazepine comprising the steps of:
a) reacting iminostilbene with alkali metal cyanate and α-hydroxy acid and
b) isolating Carbamazepine.

According to our present invention, iminostilbene is reacted with alkali metal cyanate and α-hydroxy acid in a solvent to give carbamazepine. The alkali metal cyanate is selected from sodium cyanate, potassium cyanate. α-hydroxy acid is selected from glycolic acid, lactic acid, citric acid, tartaric acid, mandelic acid or mixtures thereof. The preferred α-hydroxy acid is mandelic acid.

According to the present invention, the carbomylation reaction is carried in a solvent selected from dichloromethane, dichloroethane, toluene, hexane, heptane cyclohexane, or mixtures thereof. The preferred solvent is dichloromethane.

As per U.S. Pat. No. 6,670,472 B2, the carbomylation reaction of 10-methoxy iminostilbene carried out in various acids in presence of sodium cyanate and toluene as a solvent. The results are shown in Table-1.

TABLE 1

| | | | HPLC Analysis | | | |
|---|---|---|---|---|---|---|
| Acid used | Reflux (hours) | Conversion (%) | % of 10-methoxycarbamazepine | % of Oxo-IDB | Total Impurity | % of Unreacted 10-methoxy ISB |
| Hydrochloric acid | 4 | 89.63 | 0.24 | 70.19 | 19.19 | 10.37 |
| Sulphuric acid | 4 | 99.48 | 1.12 | 93.67 | 4.69 | 0.52 |
| Acetic acid | 12 | 59.05 | 26.22 | 12.97 | 19.86 | 40.95 |
| Monochloro-acetic acid | 12 | 96.32 | 51.5 | 24.00 | 20.82 | 3.68 |
| Ethylhexanoic acid | 22 | 44.14 | 22.86 | 12.93 | 8.35 | 55.86 |
| Benzoic acid | 12 | 98.00 | 75.50 | 9.10 | 13.40 | 2.00 |
| p-Chlorobenzoic acid | 12 | 99.66 | 56.44 | 20.00 | 23.22 | 0.34 |
| o-Chlorobenzoic acid | 12 | 98.13 | 31.25 | 54.77 | 12.11 | 1.87 |
| 2,4-Dichlorobenzoic acid | 6 | 98.48 | 55.45 | 30.04 | 12.99 | 1.52 |
| Phenylacetic acid | 6 | 72.88 | 34.38 | 18.36 | 20.14 | 27.12 |

As per the above tabulated data, the yields of 10-methoxy carbamazepine obtained are very low with high impurity levels. Unexpectedly, we have found that using α-hydroxy acid in the carbomylation reaction gave excellent purity and yields of 10-methoxy carbamazepine and carbamazepine.

The present invention provides the following major advantages:

i) Formation of impurities is less as compared to the prior art process in a carbomylation reaction due to use of α-hydroxy acid.

ii) In the carbomylation reaction, the starting material (10-methoxy iminostilbene) content is less than 1.0% as compared to the prior art processes.

iii) 10-methoxy carbamazepine content is less in hydrolysis reaction as compared to prior art process due to use of organic acid in hydrolysis stage such as oxalic acid.

iv) Yield, quality and color are improved as compared to the prior process due to formation of less impurities and degradation products.

Another aspect of the present invention provides an improved process for the preparation of Licarbazepine wherein 10-methoxyiminostilbene is reacted with alkali metal cyanate and α-hydroxy acid to give 10-methoxy carbamazepine. It is optionally subjected to crystallization in a solvent medium followed by hydrolysis to give Oxcarbazepine, which is further reacted with a reducing agent to produce Licarbazepine.

Powder X-Ray Diffraction (PXRD)

The polymorphs of the present invention are characterized by their X-ray powder diffraction pattern. Thus, the X-ray diffraction patterns of said polymorphs of the invention were measured on PANalytical, X'Pert PRO powder diffractometer equipped with goniometer of θ/θ configuration and X'Celerator detector. The Cu-anode X-ray tube was operated at 40 kV and 30 mA. The experiments were conducted over the 2θ range of 2.0°-50.0°, 0.030° step size and 50 seconds step time.

Another aspect of our invention is to prepare crystalline 10-methoxy carbamazepine having the PXRD peaks at 10.37, 10.54, 11.31, 12.88, 14.64, 19.19, 19.53, 20.60, 21.78, 22.84, 23.46, 26.47 and 27.47 degrees 2θ. Crystalline 10-methoxy carbamazepine PXRD pattern is shown in FIG. 1.

The following non-limiting examples illustrate specific embodiments of the present invention. They should not be construed as limiting the scope of present invention in any way.

EXAMPLE-1

Preparation of Oxcarbazepine a) Preparation of 10-methoxy carbamazepine from 10-methoxy iminostilbene A suspension of 10 g of 10-methoxyiminostilbene in 200 ml toluene was treated with 20 g of sodium cyanate and 39 g of mandelic acid and was heated to reflux for about 10 hrs. The reaction mixture was cooled to room temperature and charged with sodium hydroxide solution and maintained for 19 hrs. The resulting suspension was filtered, washed with water and dried to give 10 g of 10-methoxy carbamazepine.

b) Preparation of Oxcarbazepine from 10-methoxy carbamazepine 10 g of 10-methoxycabamazepine in 50 ml water and 2.4 ml of conc. HCl solution was heated to 95° C. and maintained for about 6 hrs. After completion of the reaction, the reaction mixture was cooled to room temperature and the pH was adjusted to 7.0-7.5 with sodium hydroxide solution. The resulting reaction mass was filtered and washed with ethanol and dried to produce 7 g of Oxcarbazepine.

EXAMPLE-2

Preparation of Oxcarbazepine a) Preparation of 10-methoxy carbamazepine from 10-methoxyiminostilbene A suspension of 10 g of 10-methoxyiminostilbene in 250 ml dichloromethane was treated with 17.5 g of sodium cyanate and 24 g of mandelic acid and was heated to reflux for about 6-8 hrs. The reaction mixture was cooled to room temperature and the reaction mixture was washed with distilled water and aqueous sodium bicarbonate and further the organic layer was distilled off completely. The resulting residue was treated with isopropanol; separated solid was filtered and dried to give 10-methoxy carbamazepine.

b) Preparation of Oxcarbazepine from 10-methoxy carbamazepine 100 g of 10-methoxycarbamazepine in 1000 ml water and 69.24 g of oxalic acid solution were heated to 90° C. and maintained for about 17 hrs. After completion of the reaction the reaction mixture was cooled to room temperature (RT). The resulting reaction mass was filtered and washed with 1000 ml of DM water. The wet material obtained was charged with isopropyl alcohol and DM water. The obtained reaction mixture was heated to reflux for about 2 h. The reaction mixture was cooled to 15-25° C., filtered and washed with 100 ml of IPA-water mixture. The resulting compound is dried at 60° C. for 6 h to produce 90 g of Oxcarbazepine.

EXAMPLE-4

Purification of Oxcarbazepine 100 g of Oxcarbazepine was taken in a mixture of 1350 ml of methanol and 1350 ml of MDC at 25° C. The reaction mixture was heated to reflux to obtain a clear solution and maintained for 30 minutes at reflux. The resulting suspension was filtered, washed with 1:1 mixture of MDC and methanol and the reaction mass was distilled off the reaction mass. The obtained residue was cooled to 15-20° C. and washed with chilled 1:1 mixture of MDC: methanol, filtered and dried under vacuum at 50° C. to give 90 g of Oxcarbazepine.

EXAMPLE-5

Preparation of Carbamazepine from Iminostilbene

A suspension of 10 g of iminostilbene in 100 ml toluene was treated with 20.2 g of sodium cyanate and 27.5 g of mandelic acid and was heated to reflux for about 10 hrs. The reaction mixture was cooled to room temperature and charged with sodium hydroxide solution and maintained for 8 hrs. The resulting suspension was filtered, washed with water and dried to give 11 g of carbamazepine.

We claim:

1. A process for the preparation of Oxcarbazepine which comprises the steps of:
   (a) reacting 10-methoxy iminostilbene with an alkali metal cyanate and an α-hydroxy acid in a solvent;
   (b) isolating 10-methoxy carbamazepine;
   (c) optionally crystallizing 10-methoxy carbamazepine;
   (d) hydrolyzing of 10-methoxy carbamazepine in the presence of an acid and a solvent; and
   (e) isolating Oxcarbazepine.

2. A process for the preparation of Carbamazepine, which comprises the steps of:
   (a) reacting iminostilbene with an alkali metal cyanate and an α-hydroxy acid in a solvent;
   (b) isolating Carbamazepine; and
   (c) optionally crystallizing to give pure Carbamazepine.

3. The process according to claim 1 or claim 2, wherein the alkali metal cyanate is selected from the group consisting of sodium cyanate and potassium cyanate.

4. The process according to claim 1 or claim 2, wherein the α-hydroxy acid is selected from the group consisting of glycolic acid, lactic acid, citric acid, tartaric acid, mandelic acid and mixtures thereof.

5. The process according to claim 1 or claim 2, wherein the solvent of step (a) is selected from the group consisting of dichloromethane, dichloroethane, toluene, hexane, heptanes, and cyclohexane.

6. The process according to claim 1, wherein the crystallization of step (c) is carried out with a solvent selected from the group consisting of methanol, ethanol, isopropyl alcohol and mixtures thereof.

7. The process according to claim 1, wherein the acid of step (d) is an organic acid.

8. The process according to claim 1, wherein the solvent of step (d) is selected from the group consisting of water, a water miscible organic solvent, a water immiscible organic solvent and mixtures thereof.

9. The process according to claim 8, wherein the water miscible organic solvent is selected from the group consisting of methanol, ethanol, propanol, isopropanol, butanol, t-butanol, tetrahydrofuran (THF), dimethylformamide (DMF), dimethylsulfoxide (DMSO), acetonitrile and mixtures thereof and the water immiscible organic solvent is selected from the group consisting of benzene, hexane, toluene, methylene dichloride, ethylene dichloride, chloroform, cyclohexane, xylene and mixtures thereof.

10. Crystalline 10-methoxy carbamazepine having an X-ray powder diffraction pattern characterized by peaks at 10.37, 10.54, 11.31, 12.88, 14.64, 19.19, 19.53, 20.60, 21.78, 22.84, 23.46, 26.47 and 27.47±0.2 2θ values.

11. The crystalline 10-methoxy carbamazepine according to claim 10 having a substantially similar X-ray powder diffraction pattern as depicted in FIG. 1.

12. A process for the preparation of Oxcarbazepine comprising the utilization of the crystalline 10-methoxy carbamazepine according to claim 10 or claim 11.

13. The process according to claim 7, wherein the organic acid is selected from the group consisting of oxalic acid and formic acid.

* * * * *